United States Patent
Platzek

(10) Patent No.: US 12,152,006 B2
(45) Date of Patent: Nov. 26, 2024

(54) PROCESS FOR PREPARING 4-AMINO-5-METHYLPYRIDONE

(71) Applicants: Bayer Aktiengesellschaft, Leverkusen (DE); Bayer Pharma Aktiengesellschaft, Berlin (DE)

(72) Inventor: Johannes Platzek, Berlin (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 719 days.

(21) Appl. No.: 17/435,607

(22) PCT Filed: Feb. 28, 2020

(86) PCT No.: PCT/EP2020/055297
§ 371 (c)(1),
(2) Date: Sep. 1, 2021

(87) PCT Pub. No.: WO2020/178177
PCT Pub. Date: Sep. 10, 2020

(65) Prior Publication Data
US 2022/0153701 A1    May 19, 2022

(30) Foreign Application Priority Data
Mar. 5, 2019 (EP) .................................... 19160906

(51) Int. Cl.
*C07D 213/81* (2006.01)
(52) U.S. Cl.
CPC ................................. *C07D 213/81* (2013.01)
(58) Field of Classification Search
None
See application file for complete search history.

(56) References Cited

U.S. PATENT DOCUMENTS

| 2,376,112 | A | 5/1945 | Bean et al. |
| 4,400,537 | A | 8/1983 | Weil |
| 4,609,760 | A | 9/1986 | Böhm et al. |
| 2008/0293766 | A1 | 11/2008 | Diamond et al. |
| 2022/0153699 | A1* | 5/2022 | Platzek ..................... A61P 9/00 |

FOREIGN PATENT DOCUMENTS

| CN | 103193704 | B | 3/2016 |
| DE | 570365 | C | 2/1933 |
| EP | 2075245 | A2 | 7/2009 |
| EP | 2543654 | A1 | 1/2013 |
| WO | 2005/44786 | A1 | 5/2005 |
| WO | 2008/104306 | A2 | 9/2008 |
| WO | 2008/124812 | A1 | 10/2008 |
| WO | 2016/016287 | A1 | 2/2016 |

OTHER PUBLICATIONS

Hung et al., "A General Route to 5- and 6-Substituted 4-Amino-2-oxo-1,2-dihydropyridines," Synthesis, 1984, vol. 9, p. 765-766 (Year: 1984).*
Andrus, M.B. et al., "Synthesis of resveratrol using a direct decarbonylative Heck approach from resorcylic acid," Tetrahedron Letters, 2003, 44, pp. 4819-4822.
Arnold, R.T. et al., "Thermal Rearrangement of m-Acetamidophenyl Allyl Ether," Journal of the American Chemical Society, May 1942, vol. 64, pp. 1023-1025.
Banse, H. et al., "Gegen Verbindungen der Metalle," Gmelins Handbuch Anorganischen Chemie, 1936, No. 4, pp. 490-493.
Bärfacker, L. et al., "Discovery of BAY94-8862: A Nonsteroidal Antagonist of the Mineralocorticoid Receptor for the Treatment of Cardiorenal Diseases," ChemMedChem, 2012, vol. 7, pp. 1385-1403.
Boger, D. L. et al., "An Improved Synthesis of 1,2,9,9a-Tetrahydrocyclopropa[c]benz[e]indol-4-one (CBI): A Simplified Analogue of the CC-1065 Alkylation Subunit," J. Org. Chem., 1992, 57, pp. 2873-2876.
Briner, E. et al., "Recherches sur l'obtention des amines aromatiques par voie catalytique," Helv. Chim. Acta., 1924, vol. 7, pp. 282-294.
Briner, E. et al., "Obtention des toluidines et de la phenylene-diamine," Helvetica Chimica Acta, 1926, vol. 9, pp. 956-958.
Cañete, A. et al., "Synthesis of Aminonaphthalene Derivatives Using the Bucherer Reaction Under Microwave Irradiation," Synthetic Communications, 2001, 31:14, pp. 2143-2148.
Fischer, V. F. et al., "Über die katalytische Darstellung von Anilin und seinen Homologen aus Teerphenolen and Ammoniak," Brennstoff-Chemie, 1934, vol. 15, No. 6, pp. 101-106.
Franzen, H. et al., "Mitteilungen aus dem chemischen Institut der Universität Heidelberg," Journal fur Praktische Chemie, 1908, vol. 2, pp. 143-157.
Friedlaender, P., "Verfahren zur Darstellung grauer bis schwarzer Farbstoffe," Fortschritte der Theerfarbenfabrikation und verwandter Industriezweige, 1887, vol. 2, pp. 185-186.
Herold, P. et al., "Verfahren zur Herstellung aromatischer Amine aus Oxyverbindungen der Benzolreihe," Verbindungen ohne Farbstoffcharakter: Aromatische Amine, 1933, vol. 18, pp. 446-448.
Nguyen Chi Hung et al., "A General Route to 5- and 6-Substituted 4-Amino-2-oxo-1,2-dihydropyridines," Synthesis, 1984, vol. 9, pp. 765-766.
Ikuta, M., "Metamidophenol and its Derivatives," American Chemical Journal, 1893, vol. 15, pp. 39-44.
International Preliminary Report on Patentability of PCT/EP2020/055297 (filed Feb. 28, 2020), issued by The International Bureau of WIPO on Aug. 25, 2021, 15 pages.

(Continued)

*Primary Examiner* — Jeffrey S Lundgren
*Assistant Examiner* — Anthony Joseph Seitz
(74) *Attorney, Agent, or Firm* — Quarles & Brady LLP

(57) ABSTRACT

The present invention provides a method for preparing the process intermediate 4-amino-5-methylpyridone of the formula (I), characterized in that the intermediate 4-hydroxy-5-methyl-1H-pyridin-2-one of the formula (III) is reacted with ammonia in an autoclave with addition of an ammonium bromide salt.

12 Claims, No Drawings

(56) References Cited

OTHER PUBLICATIONS

Johnson, W.S. et al., "Cyclization Studies in the Benzoquinoline Series," Journal of the American Chemical Society, Feb. 1944, vol. 66, pp. 210-215.
Letheby, "On the Utilisation of the Waste Products of the Manufacture of Coal Gas," Chemical News, August 1867, vol. 16, pp. 55-56.
Ma, J. et al., "Highly Selective Amination of o- and p-Alkyl Phenols over Pd/Al2O3—BaO," Bull. Korean Chem. Soc., 2012, vol. 33, No. 2, pp. 387-392.
Prinner, A., "V. Merz und C. Ris: o- und p-Nitranilin aus den entsprechenden Nitrophenolen," Berichete der Deutschen Chemischen Gesellschaft, 1886, vol. 19, pp. 1749-1754.
Takakura, H. et al., "Development of Luciferin Analogues Bearing an Amino Group and Their Application as BRET Donors," Chem. Asian J., 2010, 5, pp. 2053-2061.
Windaus, A. "Über einige Derivate des ac. Tetrahydro-β-naphthylamins," Chemische Berichte, 1924, vol. 57, pp. 1731-1739.
Journal of the Society of Chemical Industry, London, 1932, vol. 51; Patent List I-XXI, pp. 283 and General Notes, pp. 283-284.

\* cited by examiner

PROCESS FOR PREPARING 4-AMINO-5-METHYLPYRIDONE

This application is a U.S. national stage entry under 35 U.S.C. § 371 for International Application No. PCT/EP2020/055297, filed Feb. 28, 2020, the contents of which are incorporated herein by reference in its entirety, which claims priority to European Patent Application No. 19160906.4, filed Mar. 5, 2019.

The present invention relates to a novel and improved method for preparing 4-amino-5-methylpyridone of the formula (I)

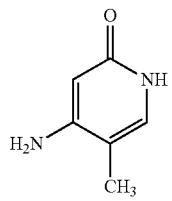

The compound of the formula (I) is a key intermediate for the preparation of finerenone (II):

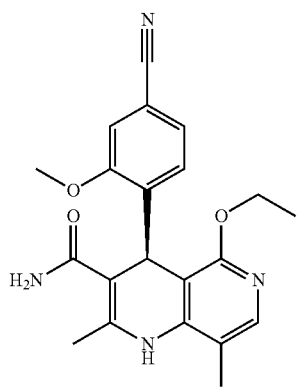

Finerenone (II) acts as a nonsteroidal antagonist of the mineralocorticoid receptor and can be used as an agent for the prophylaxis and/or treatment of cardiovascular and renal disorders such as heart failure and diabetic nephropathy.

The compound of the formula (II) and the process for the preparation thereof are described in WO 2008/104306 A1 and ChemMedChem 2012, 7, 1385 and also in WO 2016/016287 A1 (Bayer Pharma AG), both publications disclosing a detailed discussion of the research synthesis. A disadvantage of the synthesis described therein is the fact that this synthesis is unsuitable for a further industrial-scale process, since many steps proceed at very high dilution, with very high excesses of reagents, and therefore in a relatively low yield overall.

There was accordingly a need for a synthesis that can be executed on an industrial scale and that reproducibly affords the process intermediate of the formula (I) in high overall yield, with low production costs and in high purity, and that meets all regulatory requirements, in order to supply clinical trials with active substance and for use in subsequent regulatory submissions.

The preparation of compound (I) is described in Synthesis, page 765 (1984) (Example 3c). Starting from hydroxypyridone (III), which is described in Example 1c of the publication in Synthesis, reaction in boiling benzylamine (IV) affords compound (V). The benzyl group in compound (V) is then hydrolytically cleaved by catalytic hydrogenation over palladium/carbon. The overall yield over the two steps is 62.4% of theory.

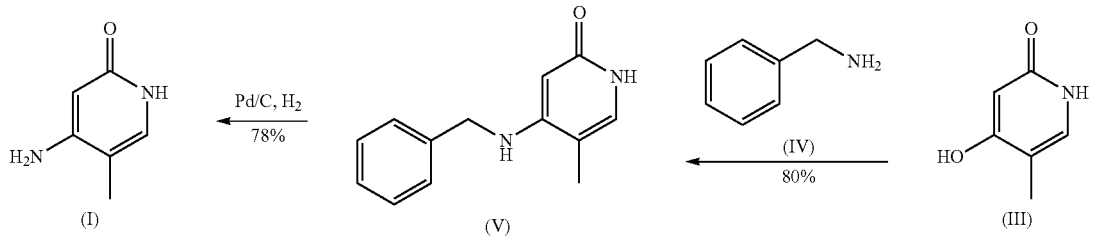

A disadvantage of the method is the use of a very large excess of benzylamine: for 30 mmol, based on the compound of the formula (III), 30 ml (275.2 mmol) is used, which is a 9.17-fold excess based on compound (III). The recycling of excess benzylamine is laborious and associated with considerable costs. The reaction is carried out in boiling benzylamine (185° C.), the reaction time is 36 hours. Such high temperatures are not practicable in standard stirred apparatuses and require special technical equipment. On repeating the procedure, by-product (VI) was in particular observed, which is attributable to traces of palladium from the precursor for (III):

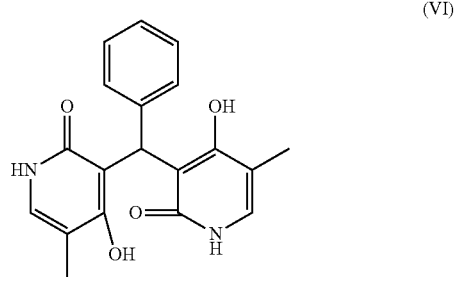 [SMILES: Cc1c[nH]c(=O)c(C(c2ccccc2)c2c(O)c(C)c[nH]c2=O)c1O]

Under the harsh reaction conditions, dehydrogenation to benzylimine occurs, which then decomposes to benzaldehyde (water is formed during the reaction), the benzaldehyde condensing with compound (III) to form compound (VI).

This by-product forms particularly on scale-up of the batches (up to >10%) and is carried over as far as compound (I). The reaction solution is worked up by cooling to room temperature, washing the precipitated crystals with methyl ethyl ketone and o-dichlorobenzene and then recrystallizing from o-dichlorobenzene. Here too, it would be advantageous to dispense with chlorinated solvents and pursue more environmentally friendly variants.

The subsequent debenzylation takes place in glacial acetic acid, 10 mmol in 200 ml, which is 2.14 g of compound (V) in 200 ml. This corresponds to a 93.45-fold excess. This means that, for 1 kg of (V), 93.45 L of acetic acid would be required. These are huge excesses that are out of the question for an industrial process. Moreover, for the conversion of 10 mmol of (V), 600 mg of Pd catalyst on carbon (10% and 30%) is used. This means that, in order to debenzylate 1 kg of compound (V), 280 g of catalyst would be necessary. This too is impractical from an industrial and economic viewpoint. For workup, the catalyst is filtered off and the filtrate evaporated to dryness, traces of acetic acid are removed by azeotroping with toluene and the residue is taken up in acetone or methyl ethyl ketone and filtered. This process is technically not feasible when upscaling, since stirred apparatuses do not evaporate to dryness. Furthermore, three different solvents are needed for the isolation. The strongly coloured reaction product is then further purified by chromatography (dichloromethane/MeOH 1:1), which is something else that would if possible need to be avoided in an industrial-scale process.

The problem addressed was therefore that of developing an alternative synthesis for the process intermediate 4-amino-5-methylpyridone as an intermediate for the preparation of the compound of the formula (II), finerenone, in particular a method that is readily executable on an industrial scale, is cost-effective and avoids large excesses of solvent, and uses reagents that are more environmentally friendly.

The use of purification steps involving chromatography should also be avoided.

With the present invention, a very efficient, shorter synthesis without the use of chromatography has been found that allows the disadvantages mentioned above to be circumvented. It has been possible to introduce the amino group into compound (III) directly, by reacting compound (III) with ammonia with the addition of an ammonium bromide salt.

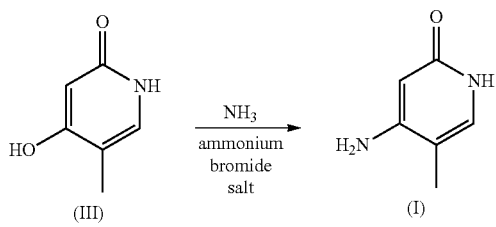

Reactions of phenols with ammonia are described in the literature: EP 2543654 A1, 2013 (Sumitomo Rubber Industries, Ltd) describes for example the reaction of phenol with ammonia at 450° C. (21.2% yield); similar processes under similarly harsh conditions are described in I.G. Farbenind. patent: DE570365, 1930; Fortschr. Teerfarbenfabr. Verw. Industriezweige, vol. 18, p. 446 and Fischer; Bahr; Wiedeking Brennstoff-Chemie, 1934, vol. 15, pp. 101, 103. Also in Chem. News J. Ind. Sci., 1867, vol. 16, p. 55; Helv. chim. Acta, 1924, vol. 7, p. 282; Gmelin Handbook: N: MVol. 2, 5.2.2, pages 490-493. Reactions specific to the chemistry of naphthalene are described in WO2008/124812 A1, 2008 and Chemistry—An Asian Journal, 2010, vol. 5, #9 pp. 2053-2061 and US 2008/293766 A1, 2008 and EP 2075245 A2, 2009 and Synthetic Communications, 2001, vol. 31, #14 pp. 2143-2148. These are special cases of the Bucherer reaction and could not be applied to compound (III), further publications thereon: Synthetic Communications, 2001, vol. 31, #14 pp. 2143-2148; Chemische Berichte, 1924, vol. 57, p. 1738. Fortschr. Teerfarbenfabr. Verw. Industriezweige, vol. 2, p. 185; WO 2005/44786 A1, 2005; Journal für Praktische Chemie (Leipzig), 1908, vol. <2>78, p. 153; Bulletin of the Korean Chemical Society, 2012, vol. 33, #2 pp. 387-392; Helvetica Chimica Acta, 1926, vol. 9, p. 957; Tetrahedron Letters, 2003, vol. 44, #26 pp. 4819-4822; US 4609760 A1, 1986; US 4400537 A1, 1983; Journal of the Society of Chemical Industry, London, 1932, vol. 51, p. 283. Journal of the American Chemical Society, 1944, vol. 66, pp. 210, 214; US 2376112, 1942; American Chemical Journal, 1893, vol. 15, p. 40. Chemische Berichte, 1886, vol. 19, p. 1751; Journal of the American Chemical Society, 1942, vol. 64, p. 1023; Journal of Organic Chemistry, 1992, vol. 57, #10 pp. 2873-2876.

All of the processes mentioned in the literature are characterized firstly by very harsh reaction conditions such as temperatures above 300° C. and in some cases by low yields. Processes that proceed with addition of sulfite or conversions according to the Bucherer reaction cannot be used for the preparation of compound (I) from (III). Moreover, no reactions of highly substituted "pyridine phenols" with ammonia have been described in the literature to date.

If compound (III) is for example reacted with ammonia gas directly in an autoclave at temperatures up to 180° C., only very low conversion into the target compound (I) is observed even after 24 hours.

It has surprisingly been found that the reaction can be carried out under much milder conditions and with almost complete conversion (generally >90% conversion) if for example 0.2 to 3 equivalents, preferably 1 equivalent, of ammonium bromide salts, for example ammonium bromide, trimethylamine-HBr, triethylamine-HBr, pyridine-HBr, lutidine-HBr or quaternary ammonium bromides, tetraalkylammonium salts such as tetramethylammonium bromide, tetrapropylammonium bromide or tetrabutylammonium bromide, are added to the reaction. Preference is given to using ammonium bromide. This is because this allows the reaction to be carried out directly in pure ammonia (as reagent and solvent). For this, an autoclave (high pressure reactor) is charged with compound (III) and one of the abovementioned bromides and 20 to 200 equivalents, preferably 40 to 100 equivalents, more preferably 40 to 60 equivalents, of ammonia are condensed in. The reaction is carried out at temperatures of 150 to 200° C., preferably 160 to 180° C., more preferably at 170° C.; the reaction times are 10 to 40, preferably 15 to 25, hours. In a particularly preferred embodiment, after the reaction has ended the excess ammonia is condensed directly into a second autoclave in which the reaction described above can then take place afresh. This ensures continuous operation of said process, with full utilization of the ammonia, i.e. ammonia losses are avoided through continuous operation. From an ecological and economic viewpoint, this has enormous advantages over the prior art method.

Once the ammonia has been evaporated off, the residue can be taken up in a suitable solvent, after which the product can be isolated and purified by crystallization. Suitable solvents are water, alcohols such as methanol, ethanol and n-butanol, and mixtures thereof with water. It is also possible for example to dissolve the product in a little acetic acid and precipitate it with a nonpolar solvent such as methyl tert-butyl ether. Preference is however given to crystallization from water (see Example 1) or, in the case of tetraalkylammonium bromides, final extraction by stirring with n-butanol (see Example 2). The isolated yields after drying are generally around 70% of theory (one chemical step) and are higher than the overall yield in the prior art over two steps (62.4% of theory, see above). The mother liquors generally still contain about 15-20% of product, which—particularly during upscaling—can also be isolated, thereby significantly increasing the overall yield to >70% of theory. Chromatographic separation, as is described in the prior art, is not required, thus making this novel inventive method very attractive as regards upscaling for production on a large scale.

The present invention therefore provides a method for preparing the process intermediate 4-amino-5-methylpyridone of the formula (I), characterized in that the intermediate 4-hydroxy-5-methyl-1H-pyridin-2-one of the formula (III) is reacted with ammonia in an autoclave with addition of an ammonium bromide salt.

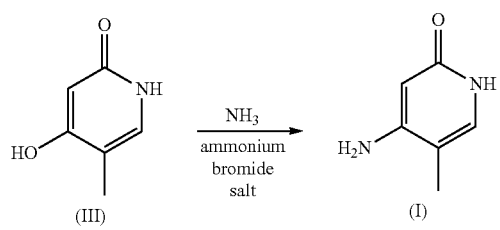

EXAMPLES

Example 1

Preparation of 4-amino-5-methyl-1H-pyridin-2-one (compound of the formula (I)) with addition of ammonium bromide A pressure reactor was charged with 4.0 g (32 mmol) of 4-hydroxy-5-methyl-1H-pyridin-2-one (compound III, prepared according to: Synthesis, p. 765 (1984)) together with 3.135 g (32 mmol) of ammonium bromide, and 27.00 g (1.585 mol) of ammonia (liquid) was then condensed in. The mixture was stirred at 170° C. for 20 hours (rise in pressure to 90 bar). For workup, the excess ammonia gas was evaporated and the residue taken up in 16 ml of water. This was then heated to 80° C., resulting in dissolution of the residue. The solution was cooled slowly and then stirred at 0-5° C. for 2 hours. The precipitated crystals were filtered off and dried overnight in a vacuum drying oven at 50° C.

Yield: 2.70 g (68.04% of theory) of a crystalline solid.
Purity approx. 98% (HPLC, 100% method)
MS (EIpos): m/z=125 [M+H]
1H-NMR (300 MHz, DMSO-d6): δ=1.81 (s, 3H), 2.54 (s, 1H), 5.24 (s, 1H), 5.79 (s, 2H), 6.85 (s, 1H), 10.27 (br s, 1H)

Example 2

Preparation of 4-amino-5-methyl-1H-pyridin-2-one (compound of the formula (I)) with addition of tetrabutylammonium bromide A pressure reactor was charged with 4.0 g (32 mmol) of 4-hydroxy-5-methyl-1H-pyridin-2-one (compound III, prepared according to: Synthesis, p. 765 (1984)) together with 10.32 g (32 mmol) of tetrabutylammonium bromide, and 27.00 g (1.585 mol) of ammonia (liquid) was then condensed in. The mixture was stirred at 170° C. for 20 hours (rise in pressure to 70 bar). For workup, the excess ammonia gas was evaporated and the residue taken up in 100 ml of water and adjusted to pH 7.0 with 1N aq. hydrochloric acid and then insoluble impurities were filtered off 100 ml of n-butanol was added and the mixture stirred at room temperature for 30 minutes. The organic phase was separated off and extracted again with 100 ml of water. The aqueous phases were combined and concentrated to dryness under reduced pressure. The residue was taken up in 10 ml of water and subjected to extractive stirring. The product was filtered off and then dried for approx. 72 hours in a vacuum drying oven at 30° C. The product thus obtained was then finally extracted by stirring with 10 ml of n-butanol, filtered and dried in a vacuum drying oven at 50° C. A crystalline solid was obtained.

Yield: 2.80 g (70.56% of theory) of a crystalline solid.
Purity approx. 98% (HPLC, 100% method)
MS (EIpos): m/z=125 [M+H]
1H-NMR (300 MHz, DMSO-d6): δ=1.81 (s, 3H), 2.54 (s, 1H), 5.24 (s, 1H), 5.79 (s, 2H), 6.85 (s, 1H), 10.27 (br s, 1H)

TABLE 1

Comparison of Examples 1 and 2 and the literature example (Synthesis, page 765, 1984, Example 3c)

| Example | Yield % of theory | Steps in synthesis | Use of Pd catalyst | By-product of the formula (VI) |
|---|---|---|---|---|
| 1 Addition of ammonium bromide | 68.04 | 1 | no | no |
| 2 Addition of tetrabutylammonium bromide | 70.56 | 1 | no | no |
| Literature example from Synthesis, page 765, 1984, Example 3c | 62.4 | 2 | yes | yes, approx. 10% of the total yield |

From what has been described above, it is clear that the methods available up to now, as described in Synthesis, page 765, 1984, Example 3c, have the disadvantages that (1) a multistep synthesis is carried out, (2) the by-product of the formula (VI) is formed (up to >10%), which occurs as an impurity in the compound of the formula (I) and needs to be removed by laborious chromatographic processes, (3) benzylamine is used in a very large excess, the recycling of which is laborious and associated with considerable costs, (4) the reaction needs to be carried out in boiling benzylamine at 185° C. and with a reaction time of 36 hours, since such high temperatures are not practicable in standard stirred apparatuses and require special technical equipment, (5) chlorinated solvents are used, which are not environmentally friendly, and (6) large amounts of Pd catalyst on carbon need to be used, the separation and processing of which is not only laborious, but also scarcely practicable in an industrial-scale synthesis.

By contrast, the method of the invention avoids these disadvantages and achieves the following effects and advantages:

(1) only one process step is carried out,
(2) the isolated yields of the compound of the formula (III) after drying are generally around 70% of theory (one chemical step) and are higher than the overall yield in the prior art over two steps (62.4% of theory, Synthesis, page 765, 1984, Example 3c),
(3) the mother liquor obtained in the process of the invention generally still contains about 15-20% of product, which—particularly during upscaling—can also be isolated, as a result of which the overall yield can be significantly increased to >70% of theory,
(4) the compound of the formula (I) is obtained in high purity as a crystalline product directly, without purification,
(5) the use of a Pd catalyst on carbon is avoided,
(6) the compound of the formula (VI) does not form as an undesired by-product,
(7) chromatographic separation, as is described in the prior art, is not required, thus making this novel inventive method very attractive as regards upscaling for production on a large scale,
(8) chromatographic purification, as is described in the prior art, is not necessary, since the undesired by-product of the formula (VI) does not form,
(9) the repeated use of solvents, in particular chlorinated solvents, can be eliminated in part or altogether, making the method of the invention much more environmentally friendly and
(10) much lower reaction times and/or lower reaction temperatures are required.

Overall, the method of the invention represents a very efficient, shorter synthesis, without the use of chromatography, that is also suitable for upscaling. It has been possible to introduce the amino group into the compound of the formula (III) directly, by reacting the compound of the formula (III) with ammonia with addition of an ammonium bromide salt.

The paragraphs that follow describe embodiments of the invention:

(1.) Method for preparing the process intermediate 4-amino-5-methylpyridone of the formula (I), characterized in that the intermediate 4-hydroxy-5-methyl-1H-pyridin-2-one of the formula (III) is reacted with ammonia in an autoclave with addition of an ammonium bromide salt.

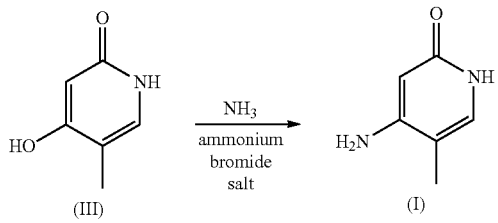

(2.) Method according to paragraph 1, characterized in that the reaction is carried out at 150° C. to 200° C.
(3.) Method according to either of paragraphs 1 or 2, characterized in that ammonium bromide is used.
(4.) Method according to any of paragraphs 1 to 3, characterized in that 1 equivalent of ammonium bromide salt is used.
(5.) Method according to any of paragraphs 1 to 4, characterized in that 20 to 200 equivalents of ammonia are used.
(6.) Method according to any of paragraphs 1 to 5, characterized in that, after the reaction has ended, the excess ammonia is condensed directly into a second autoclave in which the reaction according to paragraphs 1 to 5 is then carried out.

The invention claimed is:

1. A method for preparing the process intermediate 4-amino-5-methylpyridone of the formula (I)

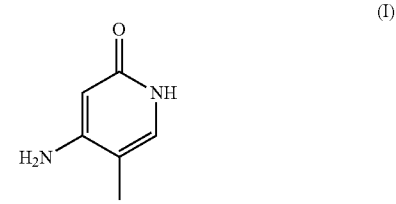

comprising reacting the intermediate 4-hydroxy-5-methyl-1H-pyridin-2-one of the formula (III)

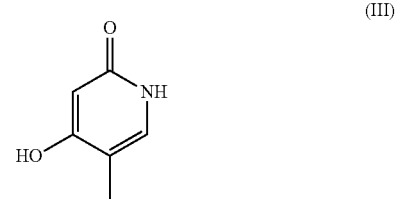

with ammonia in an autoclave with addition of an ammonium bromide salt.

2. The method according to claim 1, wherein the reaction is carried out at 150 to 200° C.

3. The method according to claim 1, wherein the reaction is carried out at 160 to 180° C.

4. The method according to claim 1, wherein the reaction is carried out at 170° C.

5. The method according to claim 1, wherein the ammonium salt is selected from the group consisting of ammonium bromide, trimethylamine-HBr, triethylamine-HBr, pyridine-HBr, lutidine-HBr, quaternary ammonium bromides, tetraalkylammonium salts, tetramethylammonium bromide, tetrapropylammonium bromide and tetrabutylammonium bromide.

6. The method according to claim 5, wherein the ammonium salt is ammonium bromide.

7. The method according to claim 6, wherein 0.2 to 3 equivalents of the ammonium bromide salt are used.

8. The method according to claim 7, wherein 1 equivalent of the ammonium bromide salt is used.

9. The method according to claim 1, wherein 20 to 200 equivalents of ammonia are used.

10. The method according to claim 1, wherein 40 to 100 equivalents of ammonia are used.

11. The method according to claim 1, wherein 40 to 60 equivalents of ammonia are used.

12. The method according to claim 1, further comprising, after the reaction has ended, condensing the excess ammonia directly into a second autoclave in which the reaction according to claim 1 is then carried out.

\* \* \* \* \*